United States Patent [19]

Goldberg

[11] 4,392,997
[45] Jul. 12, 1983

[54] ANTIGENIC PEPTIDE COMPOUNDS

[75] Inventor: Erwin Goldberg, Evanston, Ill.

[73] Assignee: Northwestern University, Evanston, Ill.

[21] Appl. No.: 389,040

[22] Filed: Jun. 16, 1982

Related U.S. Application Data

[63] Continuation-in-part of Ser. No. 280,295, Jul. 6, 1981, abandoned.

[51] Int. Cl.³ .......................................... C07C 103/52
[52] U.S. Cl. ............................................. 260/112.5 R
[58] Field of Search ................................ 260/112.5 R

[56] References Cited

U.S. PATENT DOCUMENTS 4,310,456  1/1982  Goldberg ..................... 260/112.5 R

OTHER PUBLICATIONS

Chem. Abstr., vol. 95(1981), p. 128346w.
The Journal of Biological Chemistry, vol. 254, No. 16, (1979), 7621-7623.

Primary Examiner—Delbert R. Phillips

[57] ABSTRACT

The novel antigenic peptide compounds of this invention comprise sequences of 12 to 19 amino acids, which include twelve amino acid sequence glutamic acid-glutamine-leucine-isoleucine-glutamine-asparagine-leucine-valine-proline-glutamic acid-aspartic acid-lysine, all of the amino acids being in their L-forms. The compounds have utility in vaccines for reducing the fertility of mammals.

6 Claims, No Drawings

ANTIGENIC PEPTIDE COMPOUNDS

CROSS REFERENCE

This application is a continuation-in-part of co-pending application Ser. No. 280,295, filed July 6, 1981, now abandoned.

BACKGROUND AND PRIOR ART

Mammalian spermatozoa have been known to be antigenic for many years. More recently, it has been demonstrated that mammalian sperm contain an antigenic enzyme, which is known as the $C_4$ isozyme of lactate dehydrogenase (LDH—X, LDH—$C_4$). LDH—$C_4$ has been isolated in pure crystalline form from mouse testes. Goldberg (1972) J. Biol. Chem. 247:2044-2048. The enzyme has a molecular weight of 140,000 and is composed of four identical C subunits. The amino acid sequence and three-dimensional structure of LDH—$C_4$ has been studied and partially determined by a number of investigators. See Musick et al (1976) J. Mol. Biol. 104:659-668; and Wheat et al (1977) Biochem. & Biophys. Res. Comm., 74, No. 3:1066-1077. Wheat et al determined the sequence of the essential thiol peptide from amino acid 159 to 171, and found this to be nearly identical to essential thiol peptides from other vertebrate LDH isozymes.

In 1974, Dr. Erwin Goldberg reviewed the effects of immunization with LDH—X (LDH—$C_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, makes the immunological approach to fertility control feasible." Karolinska Symposia on Research Methods in Reproductive Endocrinology, 7th Symposia: Immunological Approaches to Fertility Control, Geneva, 1974 202-222. However, such synthetic antigenic peptides remained a goal and not achievement, although their theoretical desirability has been recognized. In 1979, Dr. Erwin Goldberg summarized the state of the art as follows:

"In conclusion, and on a practical basis, immunotherapy for birth control requires more than effectiveness, specificity, reversibility, and absence of systemic side reaction. Rather large amounts of the antigen must be available in unequivocally pure form. This condition probably cannot be met by a natural product enzyme antigen from sperm or testes. Rather, contraceptive technology requires a synthesizable peptide fragment retaining antigencity and provoking a response which impairs fertility. Completion of the structural analysis of LDH—$C_4$ should allow mapping of antigenic determinants and synthesis of such peptides for use in a new contraceptive technology." "Recent advances in Reproduction and Regulation of Fertility," G. P. Talwar, editor, Elsevier/North Holland Biomedical Press (1979).

SUMMARY OF INVENTION

It has now been discovered that highly antigenic peptides can be prepared by synthesizing linear sequences of amino acids containing from 12 to 19 amino acids which include the twelve amino acid sequence: glutamic acid-glutamineleucine-isoleucine-glutamine-asparagine-leucine-valine-proline-glutamic acid-aspartic acid-lysine. All of the amino acids used to prepare these peptides are in their L-form, the sequences are arranged from N-terminal to C-terminal. Although not known with certainty, it is believed that the foregoing sequence of twelve amino acids corresponds to amino acids 5 to 16 of LDH—$C_4$. This is contrary to a recently published tentative sequence. See Musick et al (1979) J. Biol. Chem., 254, No. 16:7621-7623.

Peptide compounds embodying the antigenic sequences of this invention include the following compounds:

(a)  N—Glu—Gln—Leu—Ile—Gln—Asn—Leu—Val—Pro—Glu—Asp—Lys—C, (b)  N—Glu—Gln—Leu—Ile—Gln—Asn—Leu—Val—Pro—Glu—Asp—Lys—Leu—C, (c)  N—Glu—Gln—Leu—Ile—Gln—Asn—Leu—Val—Pro—Glu—Asp—Lys—Leu—Ser—C, (d)  N—Glu—Gln—Leu—Ile—Gln—Asn—Leu—Val—Pro—Glu—Asp—Lys—Leu—Ser—Arg—C, (e)  N—Cys—Glu—Gln—Leu—Ile—Gln—Asn—Leu—Val—Pro—Glu—Asp—Lys—C, (f)  N—Cys—Glu—Gln—Leu—Ile—Gln—Asn—Leu—Val—Pro—Glu—Asp—Lys—Leu—C, (g)  N—Cys—Glu—Gln—Leu—Ile—Gln—Asn—Leu—Val—Pro—Glu—Asp—Lys—Leu—Ser—C (h)  N—Cys—Glu—Gln—Leu—Ile—Gln—Asn—Leu—Val—Pro—Glu—Asp—Lys—Leu—Ser—Arg—C

In the foregoing formulas, the letter "N" designates the N-terminal amino acid, while the letter "C" designates the C-terminal amino acid. Gly, Gln, Leu, Ile, Asn, Val, Pro, Asp, Lys, Ser, Arg and Cys respectively represent the L-amino acid forms of glutamic acid, glutamine, leucine, isoleucine, asparagine, valine, proline, aspartic acid, lysine, serine, arginine, and cysteine.

As will be noted compounds (a) to (h) include the 12 amino acid sequence, starting with glutamine acid and ending with lysine which is believed to correspond to amino acids 5 to 16 of LDH—$C_4$. The additional amino acids of compounds (b), (c), and (d) are believed to correspond to the next amino acids of LDH—$C_4$, that is numbers 17, 18, and 19. Compound (d) therefore would contain the amino acids of the sequence 5 to 19. The compounds (e) to (h) include the same antigenic sequences, respectively, of compounds (a) to (e), but cysteine has been added at the N-terminal end to facilitate the coupling of these compounds to proteins in preparing antigenic vaccines.

The peptide compounds of the present invention can by synthesized from their constituent amino acids. For example, the synthesis can be carried out by the Merrifield solid phase method, as described in J.A.C.S. 85:2149-2154 (1963). This solid phase method for synthesizing sequences of amino acids is also described in Stewart and Young, *Solid Phase Peptide Synthesis* (W. H. Freeman and Co., San Francisco, 1969), pages 1-4. In this procedure, the C-terminal amino acid, such as lysine for compounds (a) and (e) or leucine for compounds (b) and (f), is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid, and the C-terminal amino acid is cleaved from the resin, using a suitable reagent, such as trifluoroacetic acid and hydrogen bromide. Compounds (a) to (h), as identified above, are prepared by this synthesis procedure for use in reducing the fertility of mammals.

To utilize antigenic peptides of this invention in the form of fertility reducing vaccines, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1 µMole tetanus toxoid, 60 µMoles antigenic peptide, and 18 millimoles 1-ethyl-3-(3 dimethylaminopropyl) carbodiimide hydrochloride reacted in water (pH 6) for 12 hours at room temperature and 24 hours at 4° gives a product containing 3.5 moles of peptide/mole of tetanus toxoid. Excess reactants can be removed by dialysis or gel filtration. See Pique et al, Immunochemistry, 15: 55–60 (1978). Alternatively, the peptide may be coupled using bisdiazotized benzidine (Bassiri et al, Endocrinology, 90: 722 (1972)) or glutaraldehyde.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby achieve a significant reduction in fertility. For this purpose, the amount to be administered will range from about 1 to 10 milligrams (mg) of the antigenic peptide.

The peptide compounds of this invention and their method of preparation are further illustrated by the following examples.

EXAMPLE I

Preparation of Linear Peptide
Cys—Glu—Gln—Leu—Ile—Gln—Asn—Leu—Val—Pro—Glu—Asp—Lys Synthesis of the above peptide, referred to herein as Compound (e), can be carried out employing solid phase techniques now well known in the art. In a preferred procedure amino protected lysine, representing the —COOH terminal group of the above peptide, is coupled to a conventional solid phase peptide synthesis resin such as chloromethyl polystyrene cross-linked with 1 to 2% divinyl benzene. The amino protecting group is then selectively removed utilizing a suitable reagent whose nature will depend on the protecting group used. In the preferred embodiment the t-butyloxycarbonyl (Boc) group is utilized for amino group protection and 40% trifluoroacetic acid in methylene chloride is the selective deprotecting agent.

After deprotection, the valine-resin is treated with protected aspartic acid, preferably N-Boc-O-Benzyl aspartic acid, and dicyclohexylcarbodiimide in a manner known per se as to form a peptide bond between the free amino group of the lysine residue and the carboxyl group of protected aspartic acid.

The cycle of deprotection and coupling with amino acid derivatives and dicyclohexylcarbodiimide is then repeated with the remaining amino acids in the sequence order of the above peptide. Some of the amino acids required side-chain blocking groups besides the alpha-amino protection. Such amino acids and the blocking groups are as follows:

Cys(MBzl), Glu(oBzl), Asp(oBzl), Lys(Cl-z)
Where oBzl is benzyl, Cl-z is o-chlorobenzyloxycarbonyl and MBzl is methoxybenzyl.

Completion of the synthesis provided the following peptide coupled to the styrenedivinylbenzene copolymer resin:

TFA-Cys(MBzl)Glu(oBzl)—Gln—Leu—Ile—Gln—Asn—Leu—Val—Pro—Glu(oBzl)—Asp(oBzl)—Lys(Cl—z)—Res

Decoupling of the peptide from the resin is accomplished by treatment with liquid hydrogen fluoride with concomittant cleavage of all protecting groups to produce the desired peptide.

Solid Phase Synthesis of N—Boc—Lys(Cl—z) Resin

Attachment of N—Boc—Lys(Cl—z) to chloromethyl resin was performed by the cesium salt method. A sample of chloromethyl resin (200 g.) containing 0.74 mmol chloride per gram is treated with the cesium salt of Boc—Lys—(Cl—z) resulting from the neutralization of Boc—Lysine with cesium carbonate. About 73.8 grams of Boc—Lysine is dissolved in 80% methanol and 20% water and adjusted to pH 7.0 with about 29 grams of cesium carbonate. The resulting solution is dried on a rotary evaporator, then dried three more times after three additions of 100 milliliters of xylene. To the cesium salt of Boc—Lys(Cl—z) was added 200 grams of chloromethyl resin as above and sufficient 1-Methyl-2-Pyrrolidinone to make about 1.90 liters total volume. The resulting mixture is stirred at 55° C. for 48 hours. The resin was then washed extensively with methanol, then water, then again with methanol. The resin was air dried, then dried under vacuum. After cleavage of lysine from the resin with HF, amino acid analysis gave one peak corresponding to 0.36 mmol/gm.

A sample of the resin just described (6.0 g.) was submitted to the following synthesis schedule: (1) Wash with three 100 ml. portions of methylene chloride; (2) removal of the Boc group with 40% TFA in methylene chloride for a one minute wash and for a 20 minute reaction time; (3) wash with three 100 ml. portions of methylene chloride; (4) wash with two 100 ml portions of isopropanol; (5) wash with three 100 ml. portions of methylene chloride; (6) a one minute wash and ten minutes neutrallization with 100 ml. portions of 10% triethylamine in methylene chloride; (7) wash with three portions of 100 ml. of methylene chloride; (8) Add 2.5 equivalents (7.2 mmol) of Boc amino acid and 2.5 equivalents (7.2 mmol) of dicyclohexylcarbodiimide in methylene chloride and shake for 2 hours; (9) wash with three 100 ml. portions of methylene chloride; (10) wash with two 100 ml. portions of isopropanol; (11) wash with three 100 ml. portions of methylene chloride. The above cycle was repeated for the following N-protected amino acids:

Boc—Arg(Tos)
Boc—Gly
Boc—Val
Boc—Pro
Boc—Phe
Boc—Gly
Boc—Ser(oBzl)

Boc—Ile
Boc—Gly

The protected peptide resin was submitted to deprotection to give the TFA salt of the protected peptide resin. The dried resin was stirred in the presence of 6 ml. of anisole and 60 ml. of liquid HF at 0° C. for 1 hour. The HF was removed by vacuum and the oily residue was washed with two 50 ml. portions of ethyl ether. The peptide was extracted from the resin by three 50 ml. portions of 1 molar acetic acid and the combined filtrates were lyophilized to give 8.66 grams of crude peptide. A sample (1.5 g.) was purified by 250 transfers in a counter-current distribution apparatus and recovery of the appropriate fractions gave 0.994 g. of highly purified peptide. The solvent system for the above fractionation was butanol:acetic acid:water at 4:1:5 ratios.

Amino acid analysis of the peptide after acid hydrolysis gave: $Arg_{1.00}$, $Ser_{1.03}$, $Pro_{1.01}$, $Gly_{3.05}$, $Val_{2.08}$, $Ile_{0.98}$ $Phe_{1.03}$. The peptide gave single spots in two systems with silica gel thin layer chromatography. These systems were the upper layer of butanol:acetic acid:water of 4:1:5 and the system chloroform:methanol:water of 60:30:5. The $R_f$ values for the peptide in the two systems was 0.20 and 0.32 respectively. On paper electrophoresis, the peptide gave a single spot migrating to the cathode with a $R_f$ compared to picric acid of 0.54. Electrophoresis conditions were Whatman 3MM paper with a pyridine-acetate buffer at pH 5.6.

Compounds (a) to (d) and (f) to (h) containing the same antigenic sequence as compound (e) are prepared in the same manner and characterized in the same way.

I claim:

1. The antigenic peptide compounds arranged in a sequence from N-terminal to C-terminal amino acids selected from the class consisting of:
   (a) Glu—Gln—Leu—Ile—Gln—Asn—Leu—Val—Pro—Glu—Asp—Lys
   (b) Glu—Gln—Leu—Ile—Gln—Asn—Leu—Val—Pro—Glu—Asp—Lys—Leu
   (c) Glu—Gln—Leu—Ile—Gln—Asn—Leu—Val—Pro—Glu—Asp—Lys—Leu—Ser
   (d) Glu—Gln—Leu—Ile—Gln—Asn—Leu—Val—Pro—Glu—Asp—Lys—Leu—Ser—Arg
   (e) Cys—Glu—Gln—Leu—Ile—Gln—Asn—Leu—Val—Pro—Glu—Asp—Lys
   (f) Cys—Glu—Gln—Leu—Ile—Gln—Asn—Leu—Val—Pro—Glu—Asp—Lys—Leu
   (g) Cys—Glu—Gln—Leu—Ile—Gln—Asn—Leu—Val—Pro—Glu—Asp—Lys—Leu—Ser, and
   (h) Cys—Glu—Gln'Leu—Ile—Gln—Asn—Leu—Val—Pro—Glu—Asp—Lys—Leu—Ser—Arg wherein Gly represents glycine, and Glu, Gln, Leu, Ile, Asn, Val, Pro, Asp, Lys, Ser, Arg, and Cys, respectively represent the L-amino acid forms of glutamic acid, glutamine, leucine, isoleucine, asparagine, valine, proline, aspartic acid, lysine, serine, arginine, and cysteine.

2. The peptide compounds (e) to (h) of claim 1.
3. The peptide compound (e) of claim 1.
4. The compound (f) to (i) of claim 1.
5. The peptide compound (g) of claim 1.
6. The peptide compound (h) of claim 1.

* * * * *

UNITED STATES PATENT AND TRADEMARK OFFICE
CERTIFICATE OF CORRECTION

PATENT NO. : 4,392,997
DATED : June 12, 1983
INVENTOR(S) : Erwin Goldberg

It is certified that error appears in the above-identified patent and that said Letters Patent are hereby corrected as shown below:

In column 1 of the patent following the title insert the following notice: -This invention was developed in part under Grant HD 05863 by The National Institutes of Health.-

Signed and Sealed this

Twenty-second Day of May 1984

[SEAL]

Attest:

GERALD J. MOSSINGHOFF

Attesting Officer

Commissioner of Patents and Trademarks